US012263352B2

(12) United States Patent
Lee (10) Patent No.: US 12,263,352 B2
(45) Date of Patent: Apr. 1, 2025

(54) PHOTOBIOMODULATION METHOD AND SYSTEM FOR INDUCING ACTIVITY OF BRAINDERIVED NERVE GROWTH FACTOR IN HIPPOCAMPAL TISSUE

(71) Applicant: INDUSTRY ACADEMIC COOPERATION FOUNDATION KEIMYUNG UNIVERSITY, Daegu (KR)

(72) Inventor: Jong-Ha Lee, Daegu (KR)

(73) Assignee: INDUSTRY ACADEMIC COOPERATION FOUNDATION KEIMYUNG UNIVERSITY, Daegu (KR)

( * ) Notice: Subject to any disclaimer, the term of this patent is extended or adjusted under 35 U.S.C. 154(b) by 381 days.

(21) Appl. No.: 17/737,955

(22) Filed: May 5, 2022

(65) Prior Publication Data
US 2022/0257974 A1 Aug. 18, 2022

Related U.S. Application Data

(63) Continuation of application No. PCT/KR2020/095123, filed on Sep. 24, 2020.

(30) Foreign Application Priority Data

Nov. 6, 2019 (KR) ........................ 10-2019-0140984

(51) Int. Cl.
*A61N 5/06* (2006.01)
*A61M 21/00* (2006.01)
*A61N 5/067* (2006.01)

(52) U.S. Cl.
CPC ......... *A61N 5/0622* (2013.01); *A61N 5/0618* (2013.01); *A61N 2005/0651* (2013.01);
(Continued)

(58) Field of Classification Search
CPC ....................................... A61N 5/06–2005/073
(Continued)

(56) References Cited

U.S. PATENT DOCUMENTS

2021/0113846 A1\* 4/2021 Blivet .................... A61N 2/002

FOREIGN PATENT DOCUMENTS

| KR | 102029010 B1 | 10/2019 | |
|---|---|---|---|
| KR | 102372895 B1 | 3/2022 | |
| WO | WO-2020050462 A1 \* | 3/2020 | ........... A23L 33/105 |

OTHER PUBLICATIONS

Lim et al., Differentiated HT22 cells as a novel model for in vitro screening of serotonin reuptake inhibitors, Jan. 10, 2023, Frontiers in Pharmacology, 13:1062650, pp. 1-10 (Year: 2023).*

(Continued)

*Primary Examiner* — Jonathan T Kuo
*Assistant Examiner* — Vynn V Huh
(74) *Attorney, Agent, or Firm* — STIP Law Group, LLC (57) ABSTRACT

According to a photobiomodulation method and system for inducing the activity of a brain-derived nerve growth factor in a hippocampal tissue, proposed by the present invention, a photobiomodulation (PBMT or PBM) method, which is a therapy using infrared to seat-infrared (wavelength of 600-1100 nm) light, is utilized, thereby delaying the death of cells, promoting the proliferation of meristematic cells, and inducing natural treatment without the risk of adverse reactions to a disease or lesion, in a simple and easy manner in which low-level laser light is irradiated into a living body, based on the principle that certain molecules in the living body can absorb photons and trigger signaling pathways in response to light of a specific wavelength band.

9 Claims, 8 Drawing Sheets

(52) U.S. Cl.
CPC ............... *A61N 2005/0659* (2013.01); *A61N 2005/0663* (2013.01); *A61N 5/067* (2021.08)

(58) Field of Classification Search
USPC .................................................. 607/88–94
See application file for complete search history.

(56) References Cited

OTHER PUBLICATIONS

International Search Report of PCT/KR2020/095123, Jan. 18, 2021, English translation.

Jin-Chul Heo et al, Photobiomodulation (660 nm) therapy reduces oxidative stress and induces BDNF expression in the hippocampus, Scientific Reports, Jul. 12, 2019, vol. 9, thesis No. 10114, pp. 1-8, London, United Kingdom.

Jongha Lee, Develops AI-based Alzheimer's Light Source Therapy, KMU News, Sep. 30, 2019, Keimyung University, Daegu, Republic of korea.

Kim Man-Young, Keimyung University, using light therapy to improve memory in the hippocampus, Youngnam Maeil, Sep. 19, 2019, Youngnam Mail Corp, Daegu, Republic of Korea.

Taewook Choi, Keimyung University College of Medicine, AI-based Alzheimer's Light Source Therapy Development,Youngnam Maeil, Sep. 19, 2019, Youngnam Mail Corp, Daegu, Republic of Korea.

Kim Bo-Mi, Development of AI-based light source therapy to slow down Alzheimer's dementia, Daily Clinic Journal, Sep. 18, 2019, Clinic Journal, Seoul, Republic of Korea.

\* cited by examiner

PHOTOBIOMODULATION METHOD AND SYSTEM FOR INDUCING ACTIVITY OF BRAINDERIVED NERVE GROWTH FACTOR IN HIPPOCAMPAL TISSUE

CROSS-REFERENCE TO RELATED APPLICATIONS

This application is a continuation of Application No. PCT/KR2020/095123, filed on Sep. 24, 2020 which in turn claims the benefit of Korean Patent Application No. 10-2019-0140984, filed Nov. 6, 2019, the disclosures of which are incorporated by reference into the present application.

TECHNICAL FIELD

The present invention relates to a photobiomodulation method and system for inducing activity of a brain-derived neurotrophic factor, and more particularly, to a photobiomodulation method and system for inducing activity of a brain-derived neurotrophic factor in hippocampal tissue.

BACKGROUND ART

As the social environment changes rapidly and diversifies, the brain activity for modern people is required to accept a lot of information and adapt quickly. As humans age, impairment of cognitive function and memory due to brain cell damage inevitably progresses. After middle age, symptoms such as memory deterioration, forgetfulness, and anxiety increase due to deterioration of the central nervous system appear. In the elderly, memory is deteriorated due to degenerative diseases such as dementia, which, if severe, not only makes social life impossible, but also requires enormous social costs in consideration of the impact on their families and surrounding people.

In general, it is reported that memory is carried out in three steps. First, input step of memorizing new information or knowledge into the brain, second, storage step of storing the information or knowledge into the brain, and third, recalling step of rethinking the stored information or knowledge again. If any one of the three steps is abnormal, it is said that a phenomenon in which the information or knowledge cannot be accurately remembered, that is memory deterioration, occurs.

In general, it has been reported that memory deterioration, that is, memory decline, is caused by brain cell death due to various causes such as oxidative damage in nerve cells of brain tissue, etc., resulting in memory decline. In particular, due to the decrease in brain-derived neurotrophic factor (BDNF) expression, memory and cognitive function may deteriorate and related brain diseases may occur. Treatment methods for improving memory or prevent memory decline include surgical treatment, medication treatment, or taking functional substances, etc. Surgical treatment is difficult to treat with surgery after a disease such as dementia has already occurred, so it is difficult to apply to various patients, and medication treatment may have adverse effects, so caution is required. Therefore, as a therapeutic method for improving memory and preventing memory deterioration by stimulating brain tissue, especially hippocampal tissue, there is a need to develop a photobiomodulation (PBMT or PBM) method that can induce activity of a brain-derived neurotrophic factor in hippocampal tissue.

Meanwhile, as prior arts related to the present invention, Korean patent No. 10-2029010 (Title of invention: Spatial Perception Ability and Memory Aging Prevention System through Hippocampal Stimulation, publication date: Jul. 31, 2019), etc. has been disclosed.

DISCLOSURE

Technical Problem

The present invention has been proposed to solve the above problems of the previously proposed methods. An objective of the present invention is to provide a photobiomodulation method and system for inducing activity of a brain-derived neurotrophic factor in hippocampal tissue, wherein the photobiomodulation (PBMT or PBM) method, which is a therapy using infrared or near-infrared light (wavelength of 600-1100 nm), is utilized, thereby delaying the death of cells, promoting the proliferation of meristematic cells, and inducing natural treatment without the risk of adverse reactions to a disease or lesion, etc. in a simple and easy manner in which a living body is irradiated with low-level laser, based on the principle that certain molecules in the living body can absorb photons and trigger signaling pathways in response to a specific wavelength band.

In addition, another objective of the present invention is to provide a photobiomodulation method and system for inducing activity of a brain-derived neurotrophic factor in hippocampal tissue, wherein the photobiomodulation method, which irradiates hippocampal tissue with light of a wavelength of 660 nm, is utilized, thereby suppress (A oxidative stress in the hippocampal tissue to reduce the speed of damage of hippocampal cells and to increase antioxidant enzyme expression in the hippocampal tissue, especially, the brain-derived neurotrophic factor in the hippocampal tissue is activated to improve memory and cognitive function of hippocampus and to have an excellent efficacy for the brain-related diseases such as depression or dementia, etc.

Technical Solution

According to an embodiment of the present invention to accomplish the above objectives, a photobiomodulation (PBMT or PBM) method for inducing activity of a brain-derived neurotrophic factor (BDNF) in hippocampal tissue, as a photobiomodulation method for inducing activity of a brain-derived neurotrophic factor in hippocampal tissue,
includes irradiating the hippocampal tissue with light.
Preferably, the hippocampal tissue,
may include a HT-22 cell among cells of the hippocampal tissue.
Preferably, the light irradiating the hippocampal tissue,
may be a low-level LED (Light Emitting Diode) light source.
More preferably, the light irradiating the hippocampal tissue,
may be light of infrared or near-infrared wavelength (600 nm to 1100 nm).
Even more preferably, the light irradiating the hippocampal tissue,
may be light having a wavelength of 660 nm.
Even more preferably,
when the hippocampal tissue is irradiated with the light, oxidative stress may be suppressed in the hippocampal tissue, thereby reducing hippocampal cell damage.

Even more preferably, when the hippocampal tissue is irradiated with the light, antioxidant enzyme expression may be increased in the hippocampal tissue.

Even more preferably, when the hippocampal tissue is irradiated with the light, the brain-derived neurotrophic factor (BDNF) may be activated in the hippocampal tissue.

Even more preferably, when the hippocampal tissue is irradiated with the light, the brain-derived neurotrophic factor may be activated in the hippocampal tissue, thereby improving memory and cognitive function of hippocampus.

Even more preferably, long-term memory and cognitive function of the hippocampus may be improved.

According to an embodiment of the present invention to accomplish the above objectives, a photobiomodulation (PBMT or PBM) system for inducing activity of a brain-derived neurotrophic factor (BDNF) in hippocampal tissue, as a photobiomodulation system for inducing activity of a brain-derived neurotrophic factor in hippocampal tissue, includes, a light source unit for irradiating the hippocampal tissue; and a control unit for controlling an output mode (light wavelength, light irradiation intensity, and light irradiation time) of light emitted from the light source unit.

Preferably, the hippocampal tissue, may include a HT-22 cell among cells of the hippocampal tissue.

Preferably, the light source unit, may emit a low-level LED (Light Emitting Diode) light.

More preferably, the light source unit, may emit light of infrared or near-infrared wavelength (600 nm to 1100 nm).

Even more preferably, the light source unit, may emit light having a wavelength of 660 nm.

Even more preferably, when the hippocampal tissue is irradiated with the light from the light source unit, oxidative stress may be suppressed in the hippocampal tissue, thereby reducing hippocampal cell damage.

Even more preferably, when the hippocampal tissue is irradiated with the light from the light source unit, antioxidant enzyme expression may be increased in the hippocampal tissue.

Even more preferably, when the hippocampal tissue is irradiated with the light from the light source unit, the brain-derived neurotrophic factor (BDNF) may be activated in the hippocampal tissue.

Even more preferably, when the hippocampal tissue is irradiated with the light from the light source unit, the brain-derived neurotrophic factor may be activated in the hippocampal tissue, thereby improving memory and cognitive function of the hippocampus.

Even more preferably, long-term memory and cognitive function of the hippocampus may be improved.

Advantageous Effects

According to a photobiomodulation method and system for inducing activity a brain-derived neurotrophic factor in hippocampal tissue, proposed by the present invention, the photobiomodulation (PBMT or PBM) method, which is a therapy using light of infrared or near-infrared wavelengths (600 nm to 1100 nm), is utilized, thereby delaying the death of cells, promoting the proliferation of meristematic cells, and inducing natural treatment without the risk or adverse reactions to a disease or lesion, in a simple and easy manner in which a living body is irradiated with low-level laser, based on the principle that certain molecules in the living body can absorb photons and trigger signaling pathways in response to light of a specific wavelength band.

In addition, according to a photobiomodulation method and system for inducing activity of a brain-derived neurotrophic factor in hippocampal tissue, proposed by the present invention, the photobiomodulation method, which irradiates the hippocampal tissue with light of a wavelength of 660 nm, is utilized, thereby suppress oxidative stress in the hippocampal tissue when irradiating the hippocampal tissue with light of a wavelength of 660 nm, to reduce the speed of damage of the hippocampal cell and to increase antioxidant enzyme expression in the hippocampal tissue, especially, the brain-derived neurotrophic factor in the hippocampal tissue is activated to improve memory and cognitive function of hippocampus and to have an excellent efficacy for the brain-related diseases such as depression or dementia, etc.

DESCRIPTION OF THE REFERENCE NUMERALS IN THE DRAWINGS

10: photobiomodulation system for inducing activity of a brain-derived neurotrophic factor
100: light source unit
200: control unit.

BEST MODE

Mode for Invention

Hereinafter, a preferred embodiment will be described in detail with reference to the accompanying drawings so that those of ordinary knowledge in the art to which the present invention pertains, can easily implement the present invention. However, in describing the preferred embodiment of the present invention in detail, if it is determined that a detailed description of a related known configuration or function may obscure the gist of the present invention, a detailed description thereof will be omitted. In addition, the same reference numerals are used throughout the different drawings to designate the same or similar components.

In addition, throughout the specification, when a part is connected to another part, this includes not only the case where it is directly connected, but also the case where it is indirectly connected with another device interposed therebetween. In addition, including a certain component means that other components may be further included, rather than excluding other components, unless otherwise stated.

The hippocampus is located inside the temporal lobe and occupies a part of the arc in the middle of the limbic system, and plays a role in learning, memory, recognition of new things, etc. and accepts the main afferent fiber through entorhinal cortex and send out efferent fiber through the fornix. In humans, the size of one hippocampus is usually about 3 to 3.5 $cm^3$, the diameter is about 1 cm, and the length is about 5 cm, forming a part of the arc in the middle of the limbic system. Viewed from the sagittal plane, the hippocampus is a club-shaped structure and can be divided into head, body, and tail. The hippocampus acts as an important efferent nerve fiber that transmits signals to other parts of the brain, is involved in learning and memory, can control emotional behavior and some movements, and can regulate functions of hypothalamus.

Figure 1:
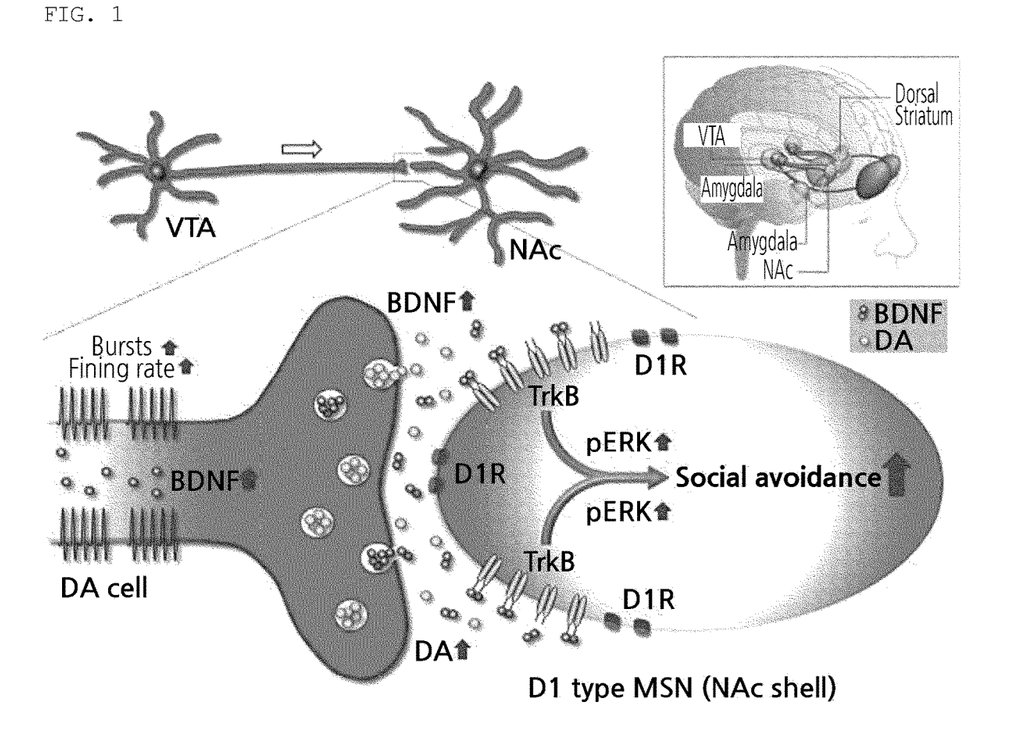
FIG. 1 is a diagram illustrating the principle that a brain-derived neurotrophic factor works.

In the hippocampus, a brain-derived neurotrophic factor (BDNF), which is involved in learning and memory, is expressed. The brain-derived neurotrophic factor acts on specific neurons in the central nervous system and peripheral nerve system to help the survival of existing neurons and prompt the growth and differentiation of new neurons and synapses. FIG. 1 is a diagram illustrating the principle that a brain-derived neurotrophic factor works. As illustrated in FIG. 1, as a protein that helps stimulate and regulate neurogenesis, the brain-derived neurotrophic factor (BDNF) itself is important for long-term memory. Studies have shown that corticosterone is known to reduce BDNF expression in mice when exposed to stress, and that persistent exposure can cause hippocampus atrophy, and in humans with depression, atrophy of the hippocampus and other limbic systems.

BDNF is known to have various efficacy on the nervous system. As a result of treatment with the antidepressant fluoxetine in post-traumatic stress disorder (PTSD)-induced mice, it can be confirmed that expression of BDNF and exercise ability are improved. An increase in BDNF expression in genetic model or cognitive deficits may result in improved social and cognitive function. In addition, in a mouse model of Alzheimer's induced by amyloid-1-42(A1-42), expression of BDNF is reduced, and administration of DNF to the hippocampus may increase cognitive function. Therefore, it can be known that BDNF, as a substance acting on the nervous system, shows excellent efficacy in the treatment of related diseases. In the case of the present invention, memory can be improved through BDNF expression in hippocampal tissue using a photobiomodulation (PBMT or PBM) method.

The photobiomodulation (PBMT or PBM) method, also called photobiomodulation, is a method of irradiating with a relatively low intensity laser of 1-500 mW in the wavelength range or 600-1100 nm, based on the principle that certain molecules of a living system can absorb photons and trigger signaling in response to light. The photobiomodulation is known to be effective nerve regeneration along with promoting wound healing, pain relief, anti-inflammatory, and anti-edema effects, and is widely applied medically such as being used in various traumatic and degenerative diseases. In the case of the present invention, various effects such as improvement of memory and cognitive function can be induced by using the photobiomodulation method that irradiates the hippocampal tissue with light of a specific wavelength.

A photobiomodulation (PBMT or PPM) method for inducing activity of a brain-derived neurological factor (BDNF) in hippocampus tissue accord to an embodiment of the present invention may be implemented including irradiating the hippocampal tissue with light.

The hippocampal tissue irradiated with light may include HT-22 cell among cells of the hippocampal tissue, and the light irradiating the hippocampal tissue may be a low-level LED (Light-Emitting Diode) light. In addition, the light irradiating the hippocampal tissue may be light of infrared or near-infrared wavelength (600 nm to 1100 nm) emitted from the LED light source as a low-level LED (Light-Emitting Diode) light source, and preferably, a wavelength of 660 nm.

A photobiomodulation method for inducing activity of a brain-derived neurological factor (BDNF) in hippocampus tissue according to an embodiment of the present invention may reduce the damage to the hippocampal cell by suppressing oxidative stress in the hippocampal tissue when irradiated with light and increase antioxidant enzyme expression in the hippocampal tissue. In addition, when the hippocampal tissue is irradiated with light, the brain-derived neurotrophic factor in the hippocampal tissue is activated thereby, improving memory and cognitive function of hippocampus and especially, improving long-term memory and cognitive function.

Hereinafter, the present invention will be described in more detail with reference to the embodiments. In the following examples, the effect of PBMT on oxidant stress in the hippocampus was evaluated. The antioxidant effect, the effect of BDNF expression, and the effect of antioxidant enzyme expression, as well as cAMP response element binding (CREB) and the effect of extracellular signal-regulated kinase (ERK) signaling pathway were evaluated by using a hippocampal cell line (HT). The following examples only illustrate the present invention and do not limit the scope of the present invention.

Examples

Materials and Methods

Antibodies and Chemicals

Antibodies to phosphorylated-cAMP response element binding (CREB) proteins (p-CREB; Ser133) and CREB (48H2) were obtained from Cell Signaling Technology, Inc. (Beverly, MA, USA); p-extracellular signal-regulated kinase (ERK) ½ (Tr202/Tyr204), ERK ½ (MK1), and BDNF (N-20) were obtained from Santa Crux Biotechnology (Santa Cruz, CA, USA). The monoclonal anti-actin antibody, methylthiazolyldiphenyl-tetrazolium bromide (MTT), and melatonin were provided by Sigma-Aldrich (St. Louis, MO, USA).

Light Condition

In the experiment, an LED-based device prototype equipment was used as a light source. The experimental group was irradiated at a wavelength of 660 nm with a power density of 20 mW/cm$^2$ (LED4D067, Torlabs Inc., Newton, New Jersey, USA). The total energy density transferred was 3 J/cm$^2$. All parameters of the laser device were selected from [Table 1].

TABLE 1

| Parameter (unit) | Value |
| --- | --- |
| Center wavelength [nm] | 660 |
| Output mode | Continue |
| Average radiant energy per unit time [mW] | 1000 |
| Irradiated area [cm$^2$] | 20 |
| Irradiance per area [mW/cm$^2$] | 20 |
| Beam profile | Round |
| Beam divergence | 90 |
| Spectral bandwidth [nm] | 25 |
| Frequency [Hz] | 2.5 |

MTT Analysis

The protection against apoptosis was analyzed using CCK-8 kit (Dojindo, Gaithersburg, MD) and MTT as follows: HT-22 cells (5×105/ml) were plated on a 96-well plate and cultured in 100 L of DMEM medium for 24 hours. Various concentrations of $H_2O_2$ were added to the cells, and the cells were cultured for 24 hours with LED irradiation of 660 nm. Then, 10 L of MTT solution (5 mg/ml MTT in PBS) was added to each well and cultured at 37° C. for 2 hours. Absorbance was measured at 450 nm and 564 nm with a Victor multi label counter (Wallac, Turku, Finland).

Preparation of Organotypic Hippocampal Slice Cultures

An organotypic hippocampal slice culture (OHC) was prepared under sterile condition using a slightly modified method. 7-week-old C57BL/6 mice were sacrificed by depilation and the scull was opened longitudinally along the middle. The hippocampus was dissected and cut in 400 m sections using a McIlwain tissue cutter (Ted Pella, Inc., Redding, CA, USA). The hippocampal slices were transferred to a dish containing dissection medium and carefully separated with a pair of sterile spatulas using a dissecting microscope. Only intact shaped sections were transferred to 0.4 m Millicell culture insert (Millipore, Billerica, MA, USA) and deposited on a 6-well plate. 4-6 slices were placed on each insert and maintained in 1 ml of serum-based medium consisting of 50% MEM-Hank medium, 25% horse serum, 25% HBSS, 5 mg/ml D-glucose, 50 mM HEPES, 2 mM L-glutamine, and 1% antibiotic/antibacterial (all obtained from GIBCO Life Technologies). During the experiment, the OHC was maintained at 37° C. in 5% of $CO_2$ and irradiated with LED light of a wavelength of 660 nm for 24 hours, and then used for histology and RNA extraction.

Reverse Transcription-Polymerase Chain Reaction (RT-PCR) and Quantitative PCR (qPCR)

All RNAs were prepared from ~100 mg of hippocampal tissue, which were dissolved in 1 ml TRIzol reagent and homogenized. All RNAs were quantified with spectrophotometers at 260 nm using NanoDrop 2000 (TermoFischer, CA, USA), and RNA quality was confirmed by 1% agarose gel electrophoresis and ethidium-bromide staining. RNA samples were stored at −80° C. until used. The cDNA was amplified with the following primers: BDNF, forward 5'-GAC AAG GCA ACT TGG CCT AC-3', and reserve 5'-CCT GTG ACA CAC GCT CAG CTC-3'; and glyceraldehyde 3-phosphate dehydrogenase (GAPDH), forward 5'-ACA TTG TTG CAA TCA ACG AC-3', and reverse 5'-ACG CCA GTA GAC TCC ACG AC-3'. The amplified product was detected using a 1% agarose gel by the Gel Doc XR System (Bio-Rad, Hercules, CA, USA). Band density is Image Lab software (version 5.0; Bio-Rad). For qPCR, the cast cDNA was mixed with Taq, dNTP (Qiagen), and SYBR Green Master Mix containing forward and reverse primer. The used prier is BDNF, forward 5'-CGA CAT CAC TGG CTG ACA CT-3', and reverse 5'-CAA GTC CGC GTC CTT ATG GT-3'; glutathione peroxidase (GPx), forward 5'-TCA CCA ACG TGG CCT CGC AAT G-3', and reverse 5'-CCT TGA TTT CTT GAT TAC TTC CTG GCT CCT G-3'; superoxide dismutasee 1 (SOD1), forward 5'-GGG TTC CAC GTG CAT CAG TAT-3', and reverse 5'-GCG GCT CCC AGC ATT TC-3'; glutathione reductase (GR), forward 5'-TGC GTG AAT GTT GGA TGT GTA CCC-3', and reverse 5'-CCG GCA TTC TCC AGT TCC TCG-3'; and h-GAPDH transfer 5'-TGG GGT GAG GCC GGT GCT GAG TAT-3', reverse 5'-CAT TGG GGG tag GAA CAC GGA AGG-3'. All experiments were implemented three times. After normalizing for the GAPDH expression level, gene expression level was analyzed. Relative gene expression data were analyzed using real-time quantitative PCR and $2^{-Cq}$ methods.

Western Blot Analysis

The level of protein expression was evaluated by Western blot analysis. Cells were dissolved and centrifuged at 16,000 g. Then, the supernatant was electrophoresed at 12% SDA-PAGE and transferred to a nitrocellulose membrane. After blocking with 5% skim milk among Tween (0.05%)/PBS for 1 hour, the membrane was detected with primary antibody and a horseradish peroxidase (HRP)-conjugated antibody. The immunoreactive band was visualized using West Femto Chemi-luminescent substrate (Thermo). Protein levels were standardized with -actin expression using ChemiDOC XRS+ (Bio-Rad, Hercules, CA, USA).

Immunohistochemistry

The hippocampus was fixed with 10% paraformaldehyde in 0.1M PBS (pH 7.4) and mounted on paraffin as described above. The tissue section was stained with hematoxylin-eosin (H&E), the general tissue shape was evaluated, and immunohistochemistry was implemented. The paraffin block was cut into 4-6 m sections and mounted on glass slides. After treating with xylene, the sections were deparaffinized by serial dilution of ethanol, stained with H&E, and then immunostained against p-ERK, p-CREB, and BDNF to label cells migrating to the hippocampus. All slides were cultured in methanol 0.3% $H_2H_2$ overnight at room temperature to quench endogenous peroxidase activity. Immunostaining was implemented overnight at 4° C. using primary antibodies diluted at 1:200-1000 with 1% bovine serum albumin (BSA) in PBS. Then, the slides were cultured with HRP-conjugated secondary antibody diluted 1:500 in 5% BSA in PBS for 1 hour at 37° C. The slides were also stained with 1% Schiff's reagent and Mayer's hematoxylin at room temperature for 5 minutes. The rate of tissue immunostaining positive cells is compared with the speed of expression of the comparison results by the third replicate.

Animal

A total of 7 7-week-old healthy C57BL/6 mice (Hyochang Science, Korea) were placed in individual cages and maintained a 12-hour light and dark cycle with food and water as needed. Efforts were made to minimize the number of animals used and to limit their suffering. Animals were anesthetized with 5% Isoflurane (JW Pharm, Korea). The anesthesia was maintained throughout the operation. All procedures were implemented in accordance with the Animal Welfare Committee's Directive 1996 on guiding principles on animal care and use. The 1996 Animal Care and Use Committee (IACUC) approval number of Keimyung University is KM201743R2.

Statistical Analysis

All data from the control group and experimental group were expressed as mean standard deviation (SD). Statistical significance was determined by Students t-test in an independent method using Microsoft Excel, and statistical significance was set to 0.05.

Ethical Approval

All experiments were approved by the Ethics Committee of Keimyung University (approval No. KM-2017-43R2).

Analysis of Results 660 nm of LED light suppresses apoptosis by reducing oxidative stress.

Figure 2:
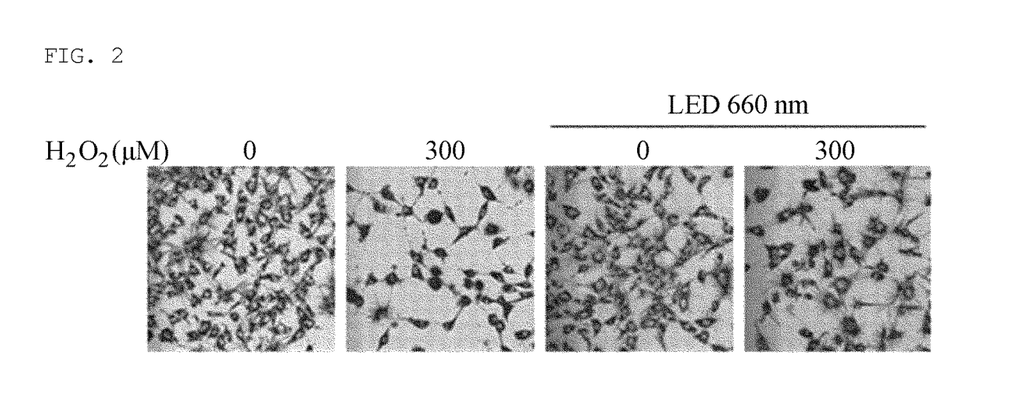
FIG. 2 illustrates confirming the apoptosis inhibitory efficacy by LED light of 660 nm during apoptosis process by oxidative stress of $H_2O_2$ using hippocampal cell line HT-22 cell using a phase contrast microscope (*$p<0.05$ and **$p<0.01$ vs control group)
Figure 3:
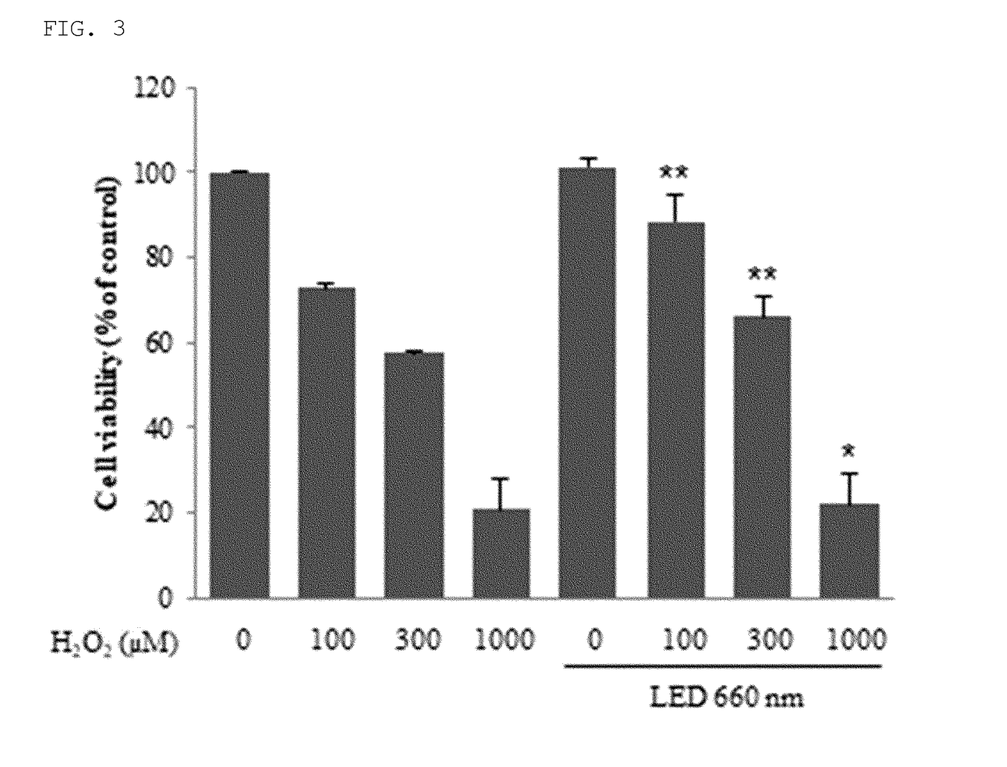
FIG. 3 is a graph illustrating the cell survival rate through MTT analysis of the apoptosis inhibitory efficacy by LED light of 660 nm during apoptosis process by oxidative stress of $H_2O_2$ using hippocampal cell line HT-22 cell (*$p<0.05$ and **$p<0.01$ vs control group)

The hippocampus HT-22 cell line was used to evaluate the effect of $H_2O_2$-induced oxidative stress on cell survival and apoptosis inhibitory effect by 660 nm of LED light (FIG. 2). After treating HT-22 cells with 100, 300, and 1000M, the cell survival rates were 72.7, 57.3, and 20.7%, respectively. In contrast, treatment with 660 nm of LED light increased cell survival rates to 88.4, 66.2, and 22.0%, respectively. In the presence of $H_2O_2$ at 100, 300, and 1000M, the percentage increases in cell survival rate were 15.7, 8.9, and 1.3% (FIG. 3). The results show that 660 nm of LED light suppresses oxidative stress caused by $H_2O_2$, which increases the survival rate of cells exposed to oxidative stress.

LED light of 660 nm increases BDNF expression in hippocampal cells through activation of ERK and CREB signaling pathways.

Figure 4:
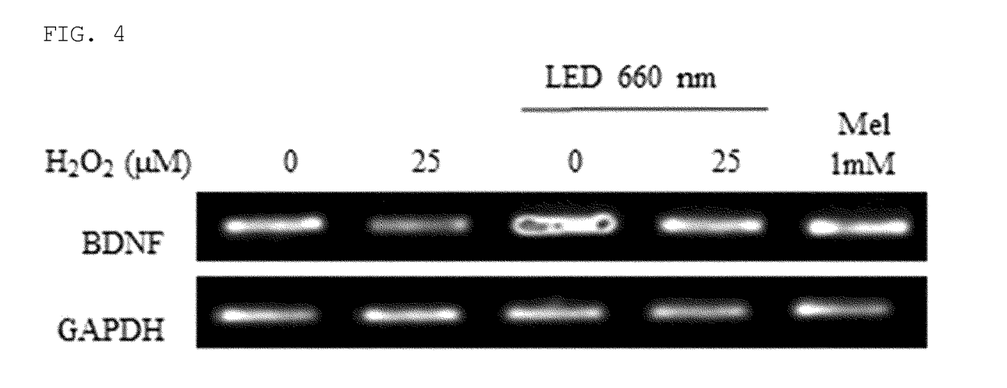
FIG. 4 illustrates confirming through PCR that BDNF is expressed when HT-22 cell is irradiated with LED light of 660 nm (*$0<0.05$ and **$p<0.01$ vs control group)
Figure 5:
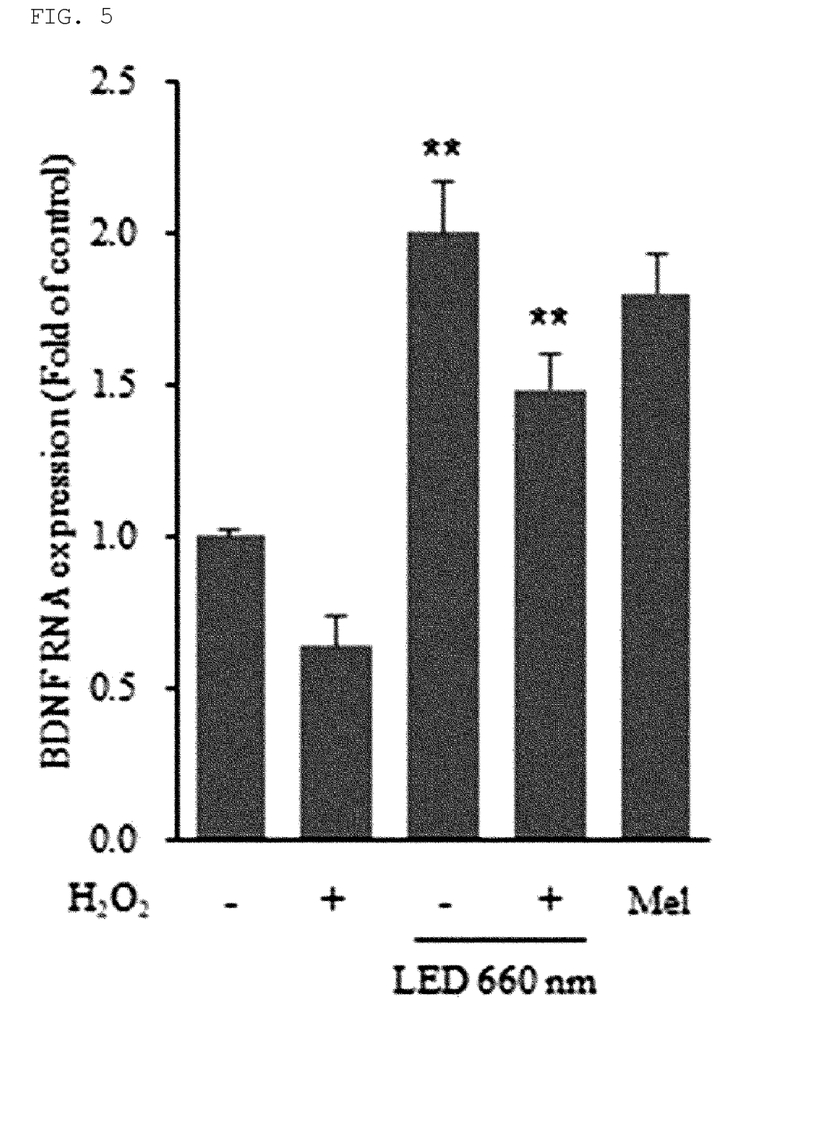
FIG. 5 is a graph illustrating the ratio of BDNF RNA expression when. HT-11 cell is irradiated with LED light of 660 nm (*$p<0$ and **$p<0.01$ vs control group)
Figure 6:
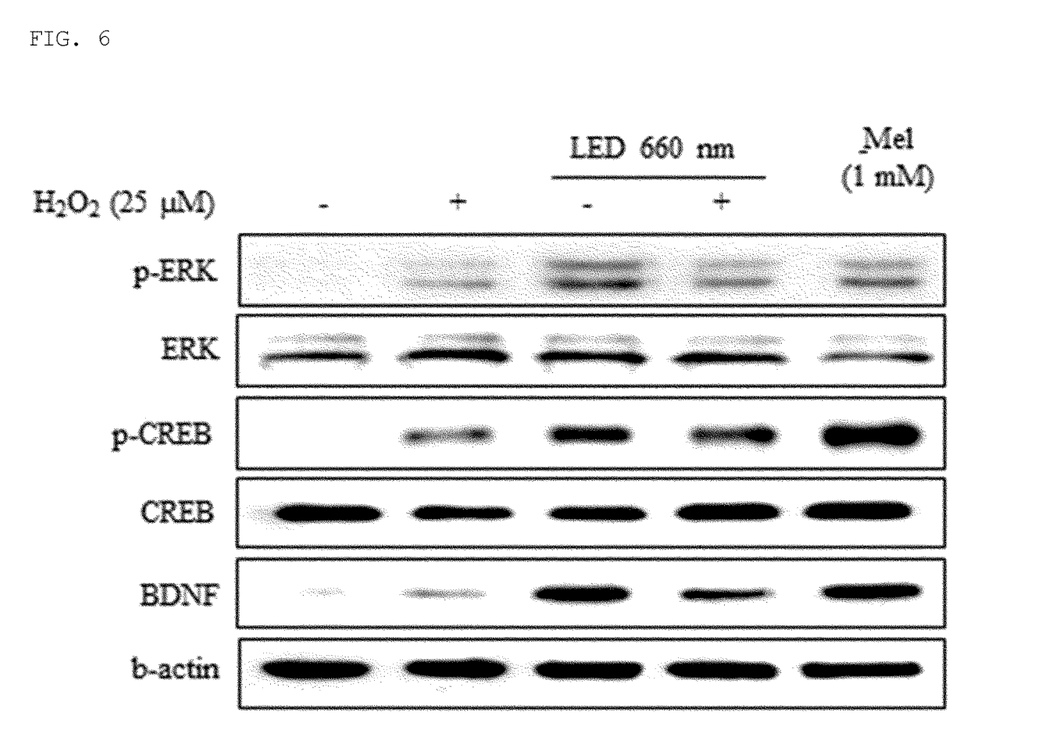
FIG. 6 illustrates confirming through Western blot analysis that the activity of p-ERK and p-CREB is increased as a result of irradiating with LED light of 660 nm to investigate the signal transmission process for BDNF expression (*$p<0.05$ and **$p<0.01$ vs control group)
Figure 7:
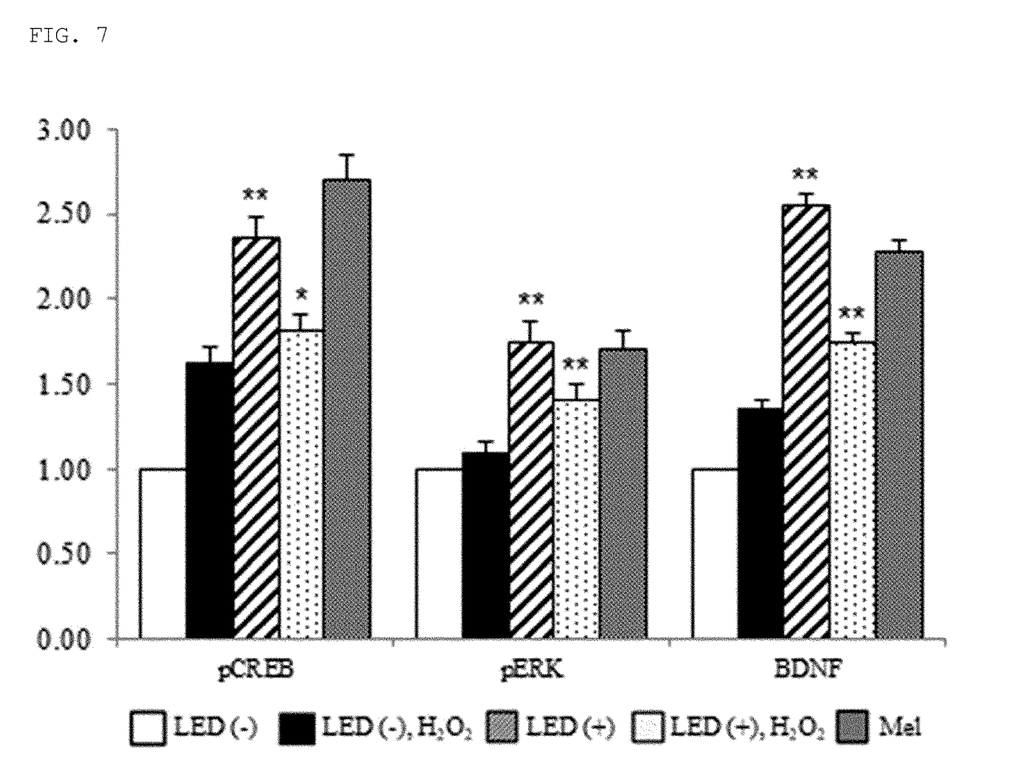
FIG. 7 is a graph illustrating the rate of p-ERK and p-CREB, and BDNF expression as a result of irradiating with LED light of 660 nm to investigate the signal transmission process for BDNF expression (*$p<0.05$ and **$p<0.01$ vs control group)

The expression of BDNF in HT-22 cell was evaluated by RT-PCR. When HT-22 cell was irradiated with LED of 660 nm, BDNF expression was approximately doubled. Although $H_2O_2$ treatment reduced BDNF expression, LED irradiation in the presence of $H_2O_2$ could still increase BDNF expression by about 2.1-fold. 1 nM of melatonin was used as a positive control (FIGS. 4 and 5). To investigate the signaling pathway leading to BDNF upregulation, ERK and CREB activation were investigated by evaluating their phosphorylation levels. It was found that phosphorylation of ERK and CREB was increased when irradiated with 660 nm of LED light. $H_2O_2$ treatment increased p-ERK and p-CREB levels, which were further increased especially when irradiated with LED light of 660 nm (FIGS. 6 and 7). These results suggest that ERK and CREB signaling pathways may mediate increased BDNF expression in HT-22 cells after irradiated with 660 nm of LED light.

LED light of 660 nm increases the expression of BDNF in the hippocampus of mice.

Figure 8:
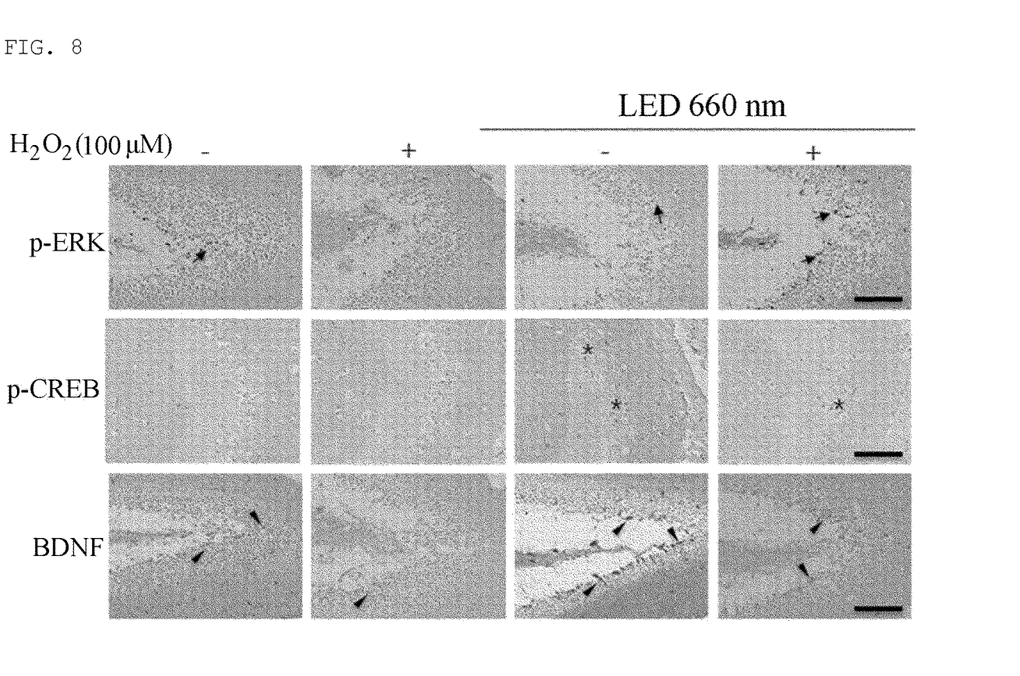
FIG. 8 illustrates confirming an increase in the number of BDNF positive cells when HT-11 cell is irradiated with LED light of 660 nm after applying oxidative stress of $H_2O_2$ (100 m) to organoid slice culture of mouse hippocampal tissue (**$p<0.01$ vs control group, scale bar=100 m)
Figure 9:
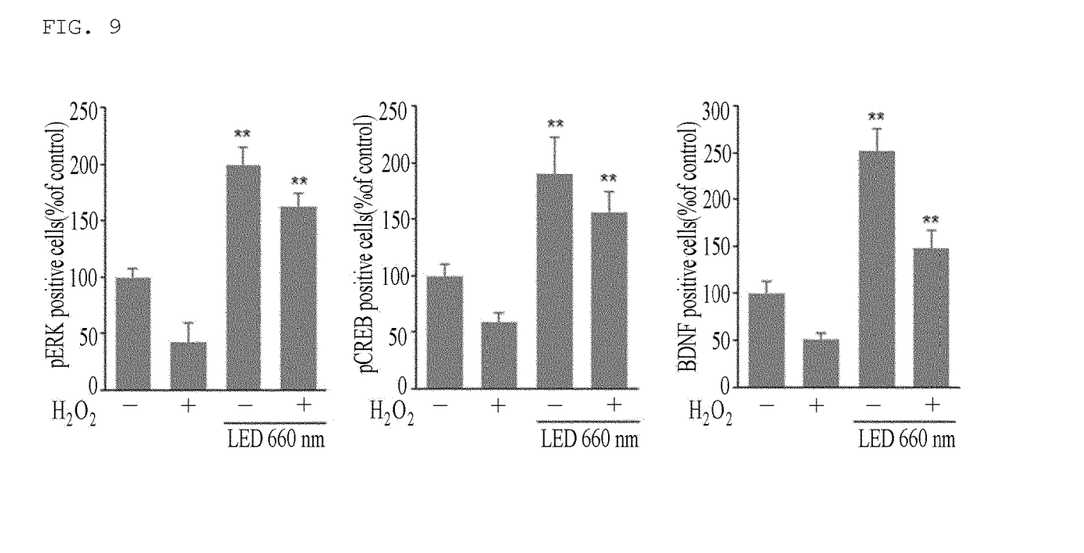
FIG. 9 is a graph illustrating the rate of p-ERK and p-CREB, and BDNF expression as a result of applying oxidative stress of $H_2O_2$ (100 m) to organoid slice culture of mouse hippocampal tissue (**$p<0.01$ vs control group)

BDNF upregulation by irradiation with LED light was confirmed in the hippocampus of mice by immunohistochemistry. The number of BDNF-expression cells was 2.5-fold and 2.8-fold higher in organotypic slice cultures of mice hippocampal tissue with LED treatment and $H_2O_2$ treatment, respectively (FIGS. 8 and 9). In addition, it was found that the numbers of p-ERK and p-CREB positive cells were higher than those without irradiation with LED light. When irradiated with LED, p-ERK-positive cells increased about 2-fold and 3.8-fold, respectively, in the presence or absence of $H_2O_2$, and p-CREB increased about 1.6-fold and 3.3-fold, respectively, under the same conditions. These results suggest that increased levels of BDNF by LED in the hippocampus may be mediated by ERK and CREB signaling pathways.

LED light of 660 nm promotes activity of antioxidant enzyme in hippocampus.

Figure 10:
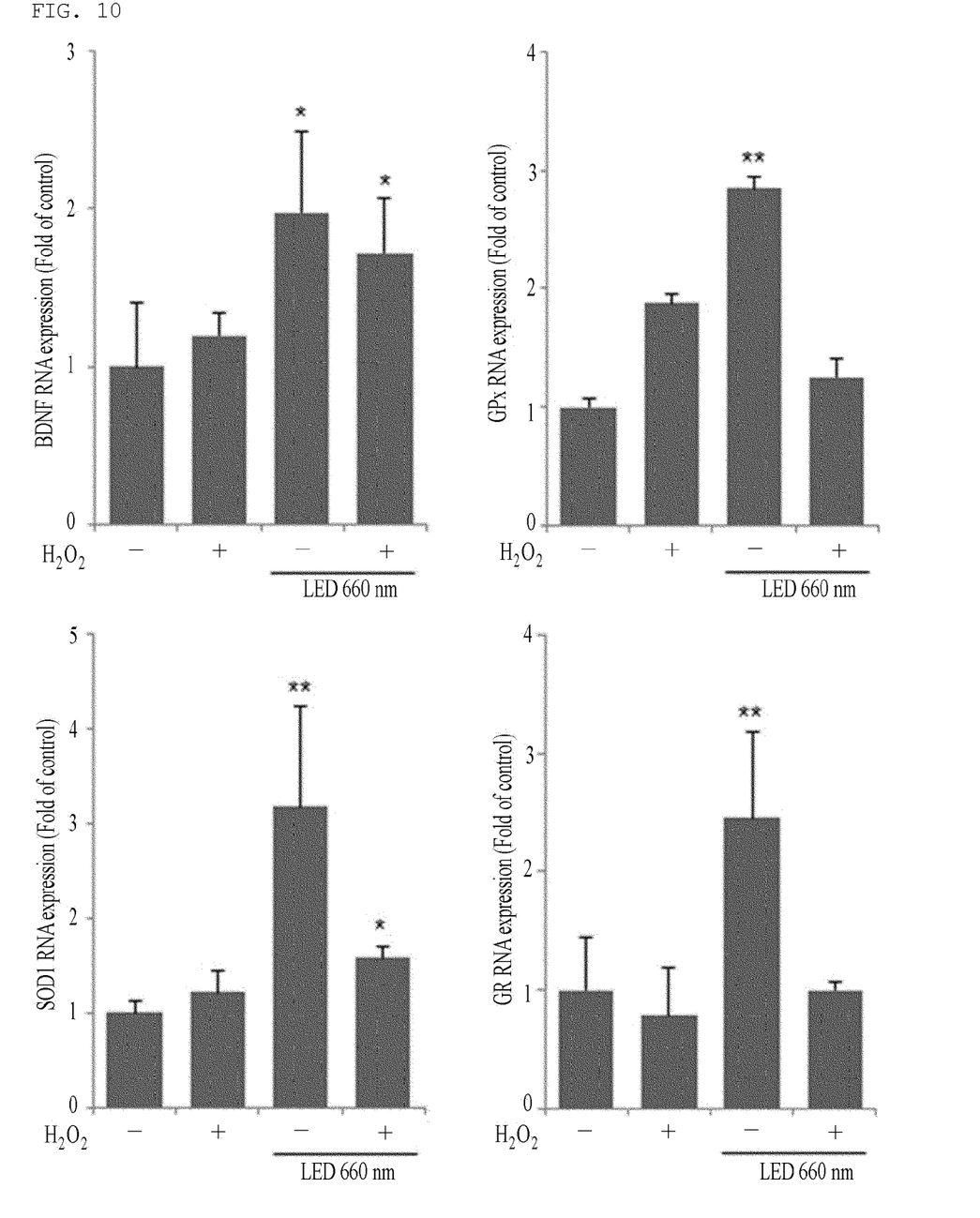
FIG. 10 is a graph illustrating an increase of the expression of antioxidant enzymes mGRX, SOD1, and mGR as the increase of BDNF expression as a result of RT-PCT analysis after applying oxidative stress of $H_2O_2$ (100 m) to organoid slice culture of mouse hippocampal tissue (**$p<0.01$ vs control group)

After irradiated with LED of 660 nm, mRNA expression of BDNF, antioxidant enzymes glutathione peroxidase (GPx), superoxide dismutase 1 (SOD1), and glutathione reductase (GR) was investigated in organotypic slice cultures of mice hippocampal tissue (FIG. 10). BDNF expression was increased in both the control group and $H_2O_2$ treated hippocampal slices when irradiated with LED. GPx expression was increased approximately 2.7-fold by irradiation with LED light. However, expression was reduced after $H_2O_2$-induced oxidative stress. Irradiation with LED light also increased SOD1 and GR levels by approximately 3-fold and 2.4-fold in control slices, and increased SOD1 levels by approximately 1.6-fold in $H_2O_2$-treated slices; In the latter case, the LED light did not affect the GR level. These results show that LED light of 660 nm induces the expression of antioxidant enzymes GPx, SOD1, and GR as well as BDNF expression in the hippocampus. In addition, 660 nm of LED light increased the expression of SOD1 according to the induction of oxidative stress by $H_2O_2$.

Argument

Photobiomodulation (PBMT or PBM) suppresses HT-22 apoptosis caused by oxidative stress and increased BDNF expression through activation of ERK and CREB signaling pathway. In addition, PBMT increased BDNF expression in organotypic slices of hippocampal tissue, increased the levels of phosphorylated ERK and CREB reduced by oxidative stress, and increased the expression of the antioxidant enzyme peroxide dismutase. These data can demonstrate that PBMT suppresses hippocampal damage induced by oxidative stress and increases the expression of BDNF, which can be used as an alternative to treat various related diseases that cause nerve damage. In other words, activation and redox homeostasis of neuron cells may be notable mechanisms of photobiomodulation using light of 660 nm.

Figure 11:
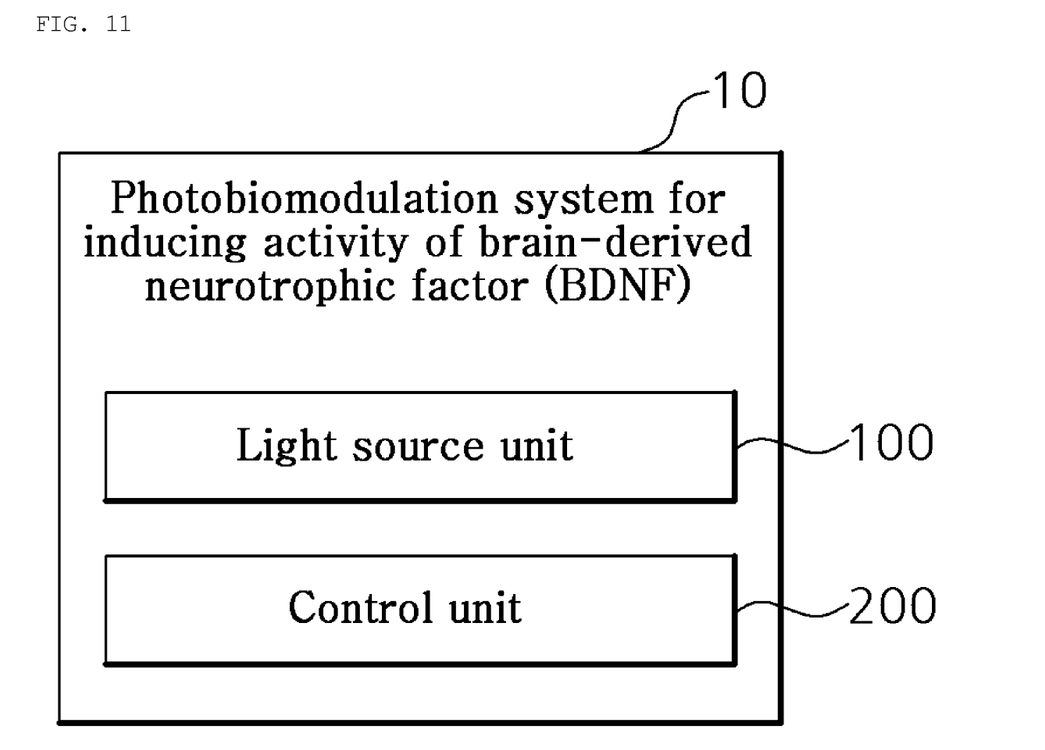
FIG. 11 is a diagram illustrating the configuration of a photobiomodulation system for inducing activity of a brain-derived neurotrophic factor as a functional block according to an embodiment of the present invention.

FIG. 11 is a diagram illustrating the configuration of a photobiomodulation system for inducing activity of a brain-derived neurotrophic factor as a functional block according to an embodiment of the present invention. As illustrated in FIG. 11, the photobiomodulation system for inducing activity of a brain-derived neurotrophic factor (10) according to an embodiment of the present invention may be implemented by including a light source unit (100) for irradiating the hippocampal tissue; and a control unit (200) for controlling an output mode (light wavelength, light irradiation intensity, and light irradiation time) of light emitted from the light source unit.

Details related to each device have been sufficiently described in relation to the photobiomodulation method for inducing activity of a brain-derived neurotrophic factor in hippocampal tissue according to an embodiment of the present invention, and thus, detailed description thereof will be omitted.

As described above, according to a photobiomodulation method and system for inducing activity of a brain-derived neurotrophic factor in hippocampal tissue, proposed by the present invention, the photobiomodulation (PBMT or PBM) method, which is a therapy using infrared or near-infrared light (wavelength of 600 to 1100 nm), is utilized, thereby delaying the death of cells, promoting the proliferation of meristematic cells, and inducing natural treatment without the of adverse reactions to a disease or lesion, in a simple and easy manner in which a living body is irradiated with low-level laser, based on the principle that certain molecules in the living body can absorb photons and trigger signaling pathways in response to light of a specific wavelength band.

In addition, according to a photobiomodulation method and system for inducing activity of a brain-derived neurotrophic factor in hippocampal tissue, proposed by the present invention, the photobiomodulation method, which irradiates the hippocampal tissue with light of a wavelength of 660 nm, is utilized, thereby suppressing oxidative stress in the hippocampal tissue when irradiated with light of a wavelength of 660 nm, to reduce the speed of damage of the hippocampal cell and to increase antioxidant enzyme expression in the hippocampal tissue, especially, the brain-derived neurotrophic factor in the hippocampal tissue is activated to improve memory and cognitive function of hippocampus and to have an excellent efficacy for the brain-related disease such as depression or dementia, etc.

The present invention described above may be modified or applied in various ways by those skilled in the art and the scope of the technical idea according to the present invention should be defined by the following claims.

The invention claimed is:

1. A photobiomodulation (PBMT or PBM) method for inducing activity of a brain-derived neurotrophic factor (BDNF) in hippocampal tissue,
  as a photobiomodulation method for inducing activity of a brain-derived neurotrophic factor in hippocampal tissue, the method comprising:
  irradiating the hippocampal tissue with light,
  wherein the hippocampal tissue includes an HT-22 cell among cells of the hippocampal tissue.

2. The method of claim 1, wherein the light irradiating the hippocampal tissue is a low-level Light Emitting Diode light.

3. The method of claim 2, wherein the light irradiating the hippocampal tissue is light of 600 nm to 1100 nm.

4. The method of claim 3, wherein the light irradiating the hippocampal tissue is light having a wavelength of 660 nm.

5. The method of claim 4, wherein when the hippocampal tissue is irradiated with the light, oxidative stress is suppressed in the hippocampal tissue, thereby reducing hippocampal cell damage.

6. The method of claim 4, wherein when the hippocampal tissue is irradiated with the light, antioxidant enzyme expression is increased in the hippocampal tissue.

7. The method of claim 4, wherein when the hippocampal tissue is irradiated with the light, the brain-derived neurotrophic factor (BDNF) is activated in the hippocampal tissue.

8. The method of claim 7, wherein when the hippocampal tissue is irradiated with the light, the brain-derived neurotrophic factor (BDNF) is activated in the hippocampal tissue, thereby improving memory and cognitive function of hippocampus.

9. The method of claim 8, wherein long-term memory and the cognitive function of the hippocampus is improved.

* * * * *